United States Patent [19]
Abe et al.

[11] Patent Number: 5,696,294
[45] Date of Patent: Dec. 9, 1997

[54] PROCESS FOR PRODUCING N,N-DIMETHYL-N-ALKYLAMINE OR N,N-DIMETHYL-N-ALKENYLAMINE

[75] Inventors: Hiroshi Abe; Hideki Taniguchi; Tetsuaki Fukushima, all of Wakayama, Japan

[73] Assignee: Kao Corporation, Tokyo, Japan

[21] Appl. No.: 716,521

[22] Filed: Sep. 19, 1996

[30] Foreign Application Priority Data

Sep. 22, 1995 [JP] Japan .................................. 7-244437

[51] Int. Cl.⁶ .................................................. C07C 209/16
[52] U.S. Cl. ............................ 564/480; 564/479; 564/509
[58] Field of Search .................................... 564/480, 479, 564/509

[56] References Cited

U.S. PATENT DOCUMENTS

| | | | |
|---|---|---|---|
| 4,293,716 | 10/1981 | Swift et al. | 564/480 |
| 4,594,455 | 6/1986 | Dudzinski | 564/463 |
| 4,625,063 | 11/1986 | Yokota et al. | 564/480 |
| 5,075,505 | 12/1991 | Forquy et al. | 564/488 |
| 5,266,730 | 11/1993 | Abe et al. | |
| 5,296,631 | 3/1994 | Abe et al. | |
| 5,530,127 | 6/1996 | Reif et al. | 544/106 |

FOREIGN PATENT DOCUMENTS

A-62-149646  7/1987  Japan .

*Primary Examiner*—Brian M. Burn
*Attorney, Agent, or Firm*—Oblon, Spivak, McClelland, Maier & Neustadt, P.C.

[57] ABSTRACT

N,N-Dimethyl-N-alkylamine or -alkenylamine is prepared by reacting a higher alcohol and dimethylamine by passing hydrogen gas and dimethylamine into a reactor containing a catalyst for the reaction at a pressure of atmospheric pressure to 100 atm. at 150° C. to 250° C. and removing water produced in the reaction as a component of the mixed hydrogen and unreacted dimethylamine gas which is discharged from the reactor, wherein at the point in the reaction at which from 90 to 99% of the higher alcohol has reacted with dimethylamine, one of the following procedures is followed: i) the introduction of only dimethylamine gas into the reactor is stopped, and the reaction is allowed to continue at a temperature 20° to 150° C. lower than the reaction temperature recited above; ii) the introduction of only dimethylamine gas into the reactor is stopped while the temperature is decreased to a level of 20° to 150° C. lower than the temperature recited above, and the reaction is allowed to proceed at the reduced temperature; or iii) the introduction of only dimethylamine gas into the reactor is stopped immediately after decreasing the temperature to a level of 20° to 150° C. lower than the temperature recited above, and the reaction is allowed to continue at the reduced temperature.

18 Claims, No Drawings

PROCESS FOR PRODUCING N,N-DIMETHYL-N-ALKYLAMINE OR N,N-DIMETHYL-N-ALKENYLAMINE

BACKGROUND OF THE INVENTION

1. Field of the Invention

The present invention relates to a process for producing an N,N-dimethyl-N-alkylamine or N,N-dimethyl-N-alkenylamine. More specifically, the invention relates to a process for producing a high quality N,N-dimethyl-N-alkylamine or N,N-dimethyl-N-alkenylamine having good hue stability.

2. Description of the Background

Aliphatic amines derived from beef tallow, coconut oil and palm oil are intermediates which are important for home and industrial applications. In particular, N,N-dimethyl-N-alkylamines or -alkenylamines are a component in the preparation of quaternary ammonium salts or other compounds and are widely used as softeners for fibers, antistatic agents and rinse based agents.

A known process for producing N,N-dimethyl-N-alkylamines or -alkenylamines is the direct amination of a higher alcohol with dimethylamine in the presence of an amination catalyst (U.S. Pat. No. 4,625,063) and JP-A-62-149646). However, products obtained by such a process are problematic in that the products themselves are colored in an acidic condition or tend to be colored when synthesized.

SUMMARY OF THE INVENTION

Accordingly, one object of the present invention is to provide a process for producing high quality N,N-dimethyl-N-alkylamine or N,N-dimethyl-N-alkenylamine which exhibits good hue stability.

Briefly, this object and other objects of the present invention as hereinafter will become more readily apparent can be attained by a process of producing N,N-dimethyl-N-alkylamine or N,N-dimethyl-N-alkenylamine by reacting a higher alcohol and dimethylamine by passing hydrogen gas and dimethylamine into a reactor containing said higher alcohol and a catalyst for the reaction at a pressure of atmospheric pressure to 100 atm. at 150° C. to 250° C. and removing water produced in the reaction as a component of the mixed hydrogen and unreacted dimethylamine gas which is discharged from the reactor, wherein at the point in the reaction at which from 90 to 99% of the higher alcohol has reacted with dimethylamine, one of the following procedures is followed:

i) the introduction of only dimethylamine gas into the reactor is stopped, and the reaction is allowed to continue at a temperature 20° to 150° C. lower than the reaction temperature recited above;

ii) the introduction of only dimethylamine gas into the reactor is stopped while the temperature is decreased to a level of 20° to 150° C. lower than the temperature recited above and the reaction is allowed to proceed at the reduced temperature; or iii) the introduction of only dimethylamine gas into the reactor is stopped immediately after decreasing the temperature to a level of 20° to 150° C. lower than the temperature recited above, and the reaction is allowed to continue at the reduced temperature.

DESCRIPTION OF THE PREFERRED EMBODIMENTS

The present inventors have found that the problem of hue stability can be solved by introducing only hydrogen gas into the reactor when the reaction of the higher alcohol reaches a certain level at which point the temperature of the reaction medium in the reactor is decreased a measured amount below the temperature at which the higher alcohol and dimethylamine are reacted.

The catalyst used in the present invention can be any amination catalyst which is conventionally used. A catalyst containing an element of group VIII is preferred in view of yield and quality of amine product. Examples of the Group VIII element include Fe, Co, Ni, Ru, Rh and Pd. Further, the catalyst used in the present invention includes those comprising copper and one of the fourth row transition metal elements (except for Cr), which catalysts may also contain one of the platinum metals of Group VIII. As the fourth row transition metal element, at least one member selected from the group consisting of nickel, cobalt and zinc is preferred, with nickel or zinc especially being preferred. Preferred platinum metals of Group VIII are platinum, palladium and ruthenium and palladium and ruthenium are particularly preferred.

In the catalyst of the present invention, the weight ratio of metal atoms of copper/the fourth row transition metal element (except for Cr)/the platinum metal of Group VIII ranges from 0.1 to 10/1/0 to 0.5. Within this range, the desired N,N-dimethyl-N-alkylamines or -alkenylamines of the present invention can be produced effectively.

Various embodiments of the catalyst of the present invention exist. One embodiment comprises two or three components of copper and a fourth row transition metal element (except for Cr) or copper, a fourth row transition metal element (except for Cr) and a platinum metal of the Group VIII. These various aspects of the catalyst exhibit an essential catalyst function in that the several components of a given catalyst mutually interact to achieve catalyst effectiveness.

An activating operation is required for the reaction of the higher alcohol with the dimethylamine gas and hydrogen gas. However, differences in metal constitution of a catalyst before the activating operation and states of the metals in a system after the activating operation are not specifically limited in the present invention except that the catalytic performance of the combination of copper and a fourth row transition metal element (except for Cr) or the combination of copper, a fourth row transition metal element (except for Cr) and a platinum metal of the Group VIII are developed by the activating operation.

In the process of the present invention, a preferred embodiment of the catalyst is the support of metal components homogeneously on an appropriate carriers in view of stabilization of the catalyst metals, stabilization being understood in terms of fixation of the active surface and endurance against catalyst poisons.

When the two or three components of copper, a fourth row transition metal element (except for Cr) and a platinum metal of the Group VIII are supported on a carrier, conventional carriers for catalysts can be used. Suitable carriers include alumina, silica-alumina, magnesia, titania, diatomaceous earth, silica, activated carbon, and natural and synthetic zeolite, and the like. The quantity of catalyst metal(s) supported on the carrier can be arbitrarily selected. However, from 5 to 70% by weight of metal based on the amount of carrier is normally preferred.

Various methods can be employed to deposit two or three component metals on a support including coprecipitation, precipitation and ion-exchange.

Examples of methods of activation of the catalyst include reduction operations using a reductant such as hydrogen gas, formalin and sodium borohydride.

The amount of catalyst used in the present invention is 0.05 to 10% by weight, preferably 0.1 to 2% by weight based on the weight of the higher alcohol.

Suitable higher alcohols used as a raw material in the present invention include linear or branched saturated or unsaturated aliphatic alcohols having 8 to 36 carbon atoms. Examples of these alcohols include octyl alcohol, lauryl alcohol, myristyl alcohol, stearyl alcohol, behenyl alcohol, oleyl alcohol and their mixtures; and branched alcohols such as Fine Oxo Alcohol 180, 180N (manufactured by Nissan Chemical Industries, Ltd.), Diadol 18G (manufactured by Mitsubishi Chemical Industries, Ltd.) and Dovanol 231 (manufactured by Mitsubishi Petrochemical Co., Ltd.).

In the present invention, it is necessary as well that hydrogen be introduced into the reaction system and that the water produced by the reaction is removed from the reaction system while the reaction is continued. The water can be removed from the reaction system either intermittently or continuously.

While a catalyst which has been prereduced, for example, with hydrogen gas, may be used in the present invention, the reduction of the catalyst may be performed by charging unreduced catalyst into the reactor together with the feedstock higher alcohol as the raw material and raising the temperature up to the reaction temperature while introducing hydrogen gas thereinto. The quantity of the hydrogen gas which is introduced can range from 1 to 100 $cm^3$/hr., preferably 10 to 50 $cm^3$/hr. per 1 g of the higher alcohol as the material. The volume mentioned is in terms of atmospheric pressure. When under a pressure of 3 atm., for example, the volume is reduced to ⅓.

In order to attain the objective of the present invention, the dimethylamine content of the gas discharged from the reaction system, which also removes water which is produced in the reaction (hereinafter referred to as exhaust gas), is controlled to within the range of 1 to 50% by volume, preferably 5 to 30% by volume.

In addition, the reaction of the present invention must be carried out at a pressure from atmospheric pressure to 100 atm. at a temperature from 150° C. to 250° C. When the pressure and temperature are within the specified range, the object of the present invention can be attained.

Furthermore, when the reaction of the higher alcohol reaches 90 to 99% of completion, preferably 93 to 98% of completion, one of the following procedures must be utilized: (1) Stopping the introduction of only the dimethylamine gas into the reaction system, decreasing temperature by 20 to 150° C. below the above reaction temperature and conducting the reaction at the lower temperature; (2) Stopping the introduction of only the dimethylamine gas into the reaction system while decreasing the reaction temperature by 20 to 150° C. below the above-mentioned reaction temperature and further continuing the reaction; or (3) Stopping the introduction of only the dimethylamine gas to the reaction system immediately after decreasing the reaction temperature by 20 to 150° C. lower than the above-mentioned temperature, and further continuing the reaction. The reduced temperature at which the reaction is continued upon temperature reduction ranges from 160 to 185° C. By this step, an N,N-dimethyl-N-alkylamine or N,N-dimethyl-N-alkenylamine having good hue stability can be obtained.

A preferred embodiment of the method of the present invention is as follows:

The higher alcohol as the raw material and catalyst are charged into a reaction vessel equipped with an inlet pipe for the hydrogen gas or nitrogen gas and a purifying column.

The quantity of the catalyst to be charged is arbitrary, but is usually in a range from 0.05 to 10% by weight based on the amount of charged alcohol. When the catalyst reduction is performed in the reaction system, the atmosphere over the reaction system is nitrogen gas. Thereafter, while introducing hydrogen gas into the reactor, the temperature is increased to the reduction temperature which is maintained for 0.5 to 3 hours. The reduction is usually carried out at 160 to 250° C. Subsequent to catalyst reduction, the prescribed reaction temperature and pressure are set with the reaction temperature being 150 to 250° C., preferably 180 to 230° and the reaction pressure ranging from atmospheric pressure to 30 atm. Thereafter, hydrogen gas is introduced into the reactor at a constant flow rate. The quantity of the hydrogen gas introduced into the reaction system is 1 to 100 $cm^3$/hour based on 1 g of the higher alcohol as a raw material.

Then, the dimethylamine is introduced into the reactor, and the reaction is started. The quantity of the dimethylamine gas introduced is adjusted so that the dimethylamine content in the exhaust gas exiting the reactor is 1 to 50% by volume. The reaction is followed by analysis with gas chromatography. When 90 to 99% of the higher alcohol is reacted, one of the following steps is performed: (1) The introduction of only dimethylamine gas into the reaction system is stopped, and then the reaction is allowed to continue at a temperature lower by 20 to 150° C. than the above reaction temperature; (2) The introduction of only the dimethylamine gas into the reaction system is stopped while decreasing the reaction temperature to a level lower by 20 to 150° than the reaction temperature mentioned above, and then further continuing the reaction; or (3) The introduction of only the dimethylamine gas into the reaction system is stopped immediately after decreasing the reaction temperature to a temperature lower by 20 to 150° C. than the reaction temperature mentioned above, and then further continuing the reaction. Preferably, the reaction is allowed to proceed at a temperature which is lower by 25 to 100° C., preferably by 30 to 50° C., than the former reaction temperature for 0.1 to 5 hours, in particular for 0.5 to 2 hours. When only the hydrogen gas is introduced, the reaction temperature needs not be kept constant and may vary within the range mentioned above. After completion of the reaction, the catalyst is removed by filtration and then the product is purified by distillation and the product N,N-dimethyl-N-alkylamine or -alkenylamine is obtained.

Having generally described this invention, a further understanding can be obtained by reference to certain specific examples which are provided herein for purposes of illustration only and are not intended to be limiting unless otherwise specified.

EXAMPLES

The procedure for preparation of the catalysts used in the Examples is described infra.

Copper-nickel (Catalyst A), copper-nickel-ruthenium (Catalyst B) and copper-zinc-ruthenium (Catalyst C) were prepared as follows.

(1) Catalyst A

Synthetic zeolite is charged into a one-liter flask. Thereto, a solution is added in which copper nitrate and nickel nitrate are dissolved in sufficient water so that the atomic weight ratio of Cu:Ni is equal to 4:1. The temperature of the mixture is raised with stirring. At the temperature of 90° C., 10% aqueous $Na_2CO_3$ solution is gradually added dropwise to the flask. After one hour aging, the precipitate is filtered, washed with water, dried at 100° C. for 10 hours, and baked at 600° C. for 3 hours. The resulting metal oxide is supported on the carrier in an amount of 50% by weight based on the carrier.

(2) Catalyst B

Titania is charged into a one-liter flask. Thereto, a solution is added in which copper nitrate, nickel nitrate and ruthenium chloride are dissolved in water so that the atomic weight ratio of Cu:Ni:Ru is equal to 5:1:0.02. The temperature of the mixture is raised with stirring. At the temperature of 90° C., a 10% aqueous $Na_2CO_3$ solution is gradually added dropwise to the flask. After one hour aging, the precipitate is filtered, washed with water, dried at 100° C. for 10 hours, and baked at 600° C. for 3 hours. The resulting metal oxide is supported on the carrier in an amount of 50% by weight based on the carrier.

(3) Catalyst C

Synthetic zeolite is charged into a one-liter flask. Thereto, a solution is added in which copper nitrate, zinc nitrate and ruthenium chloride are dissolved in water so that the atomic weight ratio of Cu:Zn:Ru is equal to 8:2:0.01. The temperature of the mixture is raised with stirring. At the temperature of 90° C., a 10% aqueous $Na_2CO_3$ solution is gradually added dropwise to the flask. After one-hour-aging, the precipitate is filtered, washed with water, dried at 100° C. for 9 hours, and baked at 600° C. for 1 hour. The resulting metal oxide is supported on the carrier in an amount of 50% by weight based on the carrier.

Examples 1 to 4 and Comparative Examples 1 and 2

1,200 g of stearyl alcohol (Kalcohi-80, manufactured by Kao Corporation) and 6 g (0.5% by weight to the alcohol as a raw material) of Catalysts A, B or C are charged into a two-liter separatory flask. While the mixture is stirred, the air in the system is replaced with nitrogen, and the temperature is increased. When the temperature reaches 100° C., hydrogen gas is passed into the system at the flow rate of 20 liters/hr. using a flow meter, and the temperature is increased to 180° C.. This temperature is maintained for 30 minutes at this level. Thereafter, the temperature is increased to 200° C. The dimethylamine gas is introduced into the flask so that the dimethylamine content in the exhaust gas passed from the flask became 20% by volume. The reaction is therefore started under atmospheric pressure. When 95% of the alcohol had reacted with dimethylamine, the introduction of dimethylamine gas is stopped. Only hydrogen gas is introduced into the flask for about 1 hour at a temperature shown in Table 1. Thereafter, the catalyst is removed by filtration, and the hue of the resulting N,N-dimethyl-N-stearylamine is determined under acid (hydrochloric acid) conditions (N,N-dimethyl-N-stearylamine:hydrochloric acid=2:1 (weight ratio)) by a Lovibond colorimeter. The results are shown in Table 1.

Comparative Examples are conducted using Catalyst A in the case where the hydrogen treatment is applied without decreasing the temperature and in the case where the hydrogen treatment is applied at the temperature of 40° C. The results are shown in Table 1.

In the hue evaluation of the present invention, the values are required to be 10 or less, preferably 5 or less.

TABLE 1

| | Kind of Catalyst | Hydrogen treatment temperature (°C.) | Hue (Lovibond Red) |
|---|---|---|---|
| Ex. 1 | Catalyst A | 170 | 3 |
| Ex. 2 | Catalyst A | 120 | 5 |
| Ex. 3 | Catalyst B | 160 | 2 |
| Ex. 4 | Catalyst C | 150 | 3 |
| Comp. Ex. 1 | Catalyst A | 200 | 20 |
| Comp. Ex. 2 | Catalyst A | 40 | 14 |

As shown by the results in Table 1, it has been found that a high quality N,N-dimethyl-N-alkylamine or N,N-dimethyl-N-alkenylamine having excellent hue stability can be produced by the process of the present invention.

Examples 5 to 7

The higher alcohols shown in Table 2 and dimethylamine are reacted in the same way as described in Example 1 in the presence of Catalyst A at the reaction temperature of 210° C. with the hydrogen treatment at 180° C. The hues of the resulting N,N-dimethyl-N-alkylamine products are determined under acid conditions in the same manner described in Example 1. The results are shown in Table 2.

TABLE 2

| | Higher alcohol | Hue (Lovibond Red) |
|---|---|---|
| Ex. 5 | Octyl alcohol | 4 |
| Ex. 6 | Lauryl alcohol | 2 |
| Ex. 7 | Isostearyl alcohol | 3 |

According to the process of the present invention, a high quality N,N-dimethyl-N-alkylamine or N,N-dimethyl-N-alkenylamine having excellent hue stability can be produced.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing N,N-dimethyl-N-alkylamine or -alkenylamine, which comprises:

reacting a higher alcohol and dimethylamine by passing hydrogen gas and dimethylamine into a reactor containing a catalyst for the reaction at a pressure of atmospheric pressure to 100 atm. at 150° C. to 250° C. and removing water produced in the reaction as a component of the mixed hydrogen and unreacted dimethylamine gas which is discharged from the reactor, wherein at the point in the reaction at which from 90 to 99% of the higher alcohol has reacted with dimethylamine, one of the following procedures is followed:

i) the introduction of only dimethylamine gas into the reactor is stopped, and the reaction is allowed to continue at a temperature 20° to 150° C. lower than the reaction temperature recited above;

ii) the introduction of only dimethylamine gas into the reactor is stopped while the temperature is decreased to a level of 20° to 150° C. lower than the temperature recited above, and the reaction is allowed to proceed at the reduced temperature; or iii) the introduction of only dimethylamine gas into the reactor is stopped immediately after decreasing the temperature to a level of 20° to 150° C. lower than the temperature recited above, and the reaction is allowed to continue at the reduced temperature.

2. The process as claimed in claim 1, in which the catalyst comprises an element of the Group VIII as an essential component.

3. The process as claimed in claim 1, wherein the weight ratio of metal atoms of copper/the fourth row transition metal except for Cr/the platinum metal of the Group VIII is in the range of 0.1 to 10/1/0 to 0.5 in the catalyst.

4. The process as claimed in claim 1, which further comprises, prior to introducing both hydrogen and dimethylamine gas into the reactor, passing only hydrogen into the reaction at a temperature lower by 25° to 100° C. relation to the reactor temperature at the time of introduction of both hydrogen and dimethylamine gas into the reactor.

5. The process as claimed in claim 1, wherein the quantity of the hydrogen gas introduced into the reaction system is 1 to 100 cm$^3$/hr. based on 1 g of the higher alcohol as a raw material.

6. The process as claimed in claim 1, wherein, as a mixture of hydrogen and dimethylamine gas, as an exhaust gas, passes out of the reactor, the amount of dimethylamine in the exhaust gas is adjusted to 1 to 50 vol. %.

7. The process as claimed in claim 6, wherein the exhaust gas removes water produced by the reaction from the system.

8. The process as claimed in claim 3, wherein the fourth row transition metal is nickel, zinc or cobalt.

9. The process as claimed in claim 3, wherein the catalytically active metals are supported on a carrier selected from the group consisting of alumina, silica-alumina, magnesia, titania, diatomaceous earth, silica, activated carbon or a natural or synthetic zeolite.

10. The process as claimed in claim 9, wherein from 5 to 70% by wt. of the metal is supported on the carrier.

11. The process as claimed in claim 1, wherein the higher alcohol is octyl alcohol, lauryl alcohol, myristyl alcohol, stearyl alcohol, behenyl alcohol, oleyl alcohol, or mixtures thereof or mixed branched aliphatic alcohols.

12. The process as claimed in claim 1, wherein said amount of hydrogen gas ranges from 10 to 50 cm$^3$/hr. per 1 gram of alcohol.

13. The process as claimed in claim 6, wherein said concentration of dimethylamine in the exhaust gas ranges from 5 to 30 vol. %.

14. The process as claimed in claim 1, wherein the reaction temperature ranges from 180 to 230° C.

15. The process as claimed in claim 1, wherein the temperature is reduced by 25° to 100° C. in the three process alternatives at the near completion of the reaction.

16. The process as claimed in claim 15, wherein the extent of temperature reduction ranges from 30° to 50° C.

17. The process as claimed in claim 1, wherein the period of reaction at the near completion of the reaction ranges from 0.1 to 5 hours.

18. The process as claimed in claim 17, wherein said period of reaction ranges from 0.5 to 2 hours.

* * * * *